US008257263B2

United States Patent
Ikegame et al.

(10) Patent No.: US 8,257,263 B2
(45) Date of Patent: Sep. 4, 2012

(54) ULTRASONIC DIAGNOSTIC APPARATUS AND ULTRASONIC PROBE

(75) Inventors: Haruka Ikegame, Kaisei-machi (JP); Youichi Nakamura, Kaisei-machi (JP)

(73) Assignee: Fujifilm Corporation (JP)

( * ) Notice: Subject to any disclaimer, the term of this patent is extended or adjusted under 35 U.S.C. 154(b) by 712 days.

(21) Appl. No.: 12/486,401

(22) Filed: Jun. 17, 2009

(65) Prior Publication Data

US 2009/0312643 A1 Dec. 17, 2009

(30) Foreign Application Priority Data

Jun. 17, 2008 (JP) ................................. 2008-157625

(51) Int. Cl.
*A61B 8/00* (2006.01)
(52) U.S. Cl. .......................... 600/459; 600/437; 600/443
(58) Field of Classification Search .................. None
See application file for complete search history.

(56) References Cited

U.S. PATENT DOCUMENTS

| 4,444,197 | A | * | 4/1984 | Koyano et al. ................ 600/443 |
| 6,171,248 | B1 | * | 1/2001 | Hossack et al. ............... 600/459 |
| 2002/0148277 | A1 | * | 10/2002 | Umeda ......................... 73/1.82 |

FOREIGN PATENT DOCUMENTS

JP 2000-201936 7/2000
* cited by examiner

*Primary Examiner* — Long V. Le
*Assistant Examiner* — Farshad Negarestan
(74) *Attorney, Agent, or Firm* — Studebaker & Brackett PC; Donald R. Studebaker

(57) ABSTRACT

An ultrasonic probe having a combination of plural types of functions and thereby easy to carry. The ultrasonic probe includes: a housing part for housing a first group of ultrasonic transducers and a second group of ultrasonic transducers in a first edge part and a second edge part having different curvatures from each other, respectively, the first and second groups of ultrasonic transducers transmitting ultrasonic waves according to drive signals and receiving ultrasonic echoes to output reception signals; and a grip part rotatable relative to the housing part.

5 Claims, 7 Drawing Sheets

FIG.9B

ULTRASONIC DIAGNOSTIC APPARATUS AND ULTRASONIC PROBE

CROSS-REFERENCE TO RELATED APPLICATION

The present application claims priority from Japanese Patent Application No. 2008-157625 filed on Jul. 17, 2008, the contents of which are incorporated herein by reference in their entirety.

BACKGROUND OF THE INVENTION

1. Field of the Invention

The present invention relates to an ultrasonic diagnostic apparatus for imaging organs within a living body and so on by transmitting and receiving ultrasonic waves to generate ultrasonic images to be used for diagnoses. Further, the present invention relates to an ultrasonic probe to be used in the ultrasonic diagnostic apparatus.

2. Description of a Related Art

In medical fields, various imaging technologies have been developed for observation and diagnoses within an object to be inspected. Especially, ultrasonic imaging for acquiring interior information of the object by transmitting and receiving ultrasonic waves enables image observation in real time and provides no exposure to radiation unlike other medical image technologies such as X-ray photography or RI (radio isotope) scintillation camera. Accordingly, ultrasonic imaging is utilized as an imaging technology at a high level of safety in a wide range of departments including not only the fetal diagnosis in obstetrics but also gynecology, circulatory system, digestive system, and so on.

Conventionally, a mainstream ultrasonic diagnostic apparatus has been large-scaled and provided in an examination room for exclusive use. It has been necessary to move examinees to the examination room provided with the ultrasonic diagnostic apparatus at each time of ultrasonic diagnosis, and significant burden has been imposed on the examinees. In order to reduce the burden on the examinees, an ultrasonic diagnostic apparatus is required that is easily carried and used by an operator (diagnostician) who operates the ultrasonic diagnostic apparatus. When the ultrasonic diagnostic apparatus is carried and used, for example, the operator selectively uses one of a linear probe in which a large contact area with a surface of the object can be taken and a convex probe in which a wide imaging range can be taken instead of a large contact area with a surface of the object. Accordingly, it is necessary to carry plural ultrasonic probes at a time, and there is a problem of complicated transportation.

As a related technology, Japanese Patent Application Publication JP-P2000-201936A discloses an ultrasonic imaging probe capable of generating at least two ultrasonic imaging surfaces. Specifically, the ultrasonic imaging probe includes a leading end radiation convertor for generating a first imaging surface and a side radiation convertor for generating a second imaging surface, and the first imaging surface and the second imaging surface are orthogonal to each other.

However, the ultrasonic imaging probe disclosed in JP-P2000-201936A is for watching a tool such as a biopsy needle on the two ultrasonic imaging surfaces at the same time, but plural types of functions are not provided to one ultrasonic probe.

SUMMARY OF THE INVENTION

The present invention has been achieved in view of the above-mentioned problems. A purpose of the present invention is to provide an ultrasonic probe having a combination of plural types of functions and thereby easy to carry, and an ultrasonic diagnostic apparatus employing the ultrasonic probe.

In order to accomplish the above mentioned purpose, an ultrasonic probe according to one aspect of the present invention includes: a housing part for housing a first group of ultrasonic transducers and a second group of ultrasonic transducers in a first edge part and a second edge part having different curvatures from each other, respectively, the first and second groups of ultrasonic transducers transmitting ultrasonic waves according to drive signals and receiving ultrasonic echoes to output reception signals; and a grip part rotatable relative to the housing part.

Further, an ultrasonic diagnostic apparatus according to one aspect of the present invention includes: an ultrasonic probe including a housing part for housing a first group of ultrasonic transducers and a second group of ultrasonic transducers in a first edge part and a second edge part having different curvatures from each other, respectively, the first and second groups of ultrasonic transducers transmitting ultrasonic waves according to drive signals and receiving ultrasonic echoes to output reception signals, a grip part rotatable relative to the housing part, and a detecting unit for detecting whether an axis direction of said housing part is at a first predetermined angle or a second predetermined angle relative to an axis direction of the grip part; and an ultrasonic diagnostic apparatus main body for selectively generating one of a first group of drive signals for driving the first group of ultrasonic transducers and a second group of drive signals for driving the second group of ultrasonic transducers according to a detection result of the detecting unit.

According to the one aspect of the present invention, the grip part is rotatable relative to the housing part for housing the first group of ultrasonic transducers and the second group of ultrasonic transducers in the first edge part and the second edge part having different curvatures from each other, respectively, and therefore, an ultrasonic probe having a combination of plural types of functions and thereby easy to carry can be provided. Further, an ultrasonic diagnostic apparatus including the ultrasonic probe can be provided.

DESCRIPTION OF THE PREFERRED EMBODIMENTS

Hereinafter, embodiments of the present invention will be explained in detail with reference to the drawings. The same reference numerals are assigned to the same component elements and the explanation thereof will be omitted.

Figure 1A:
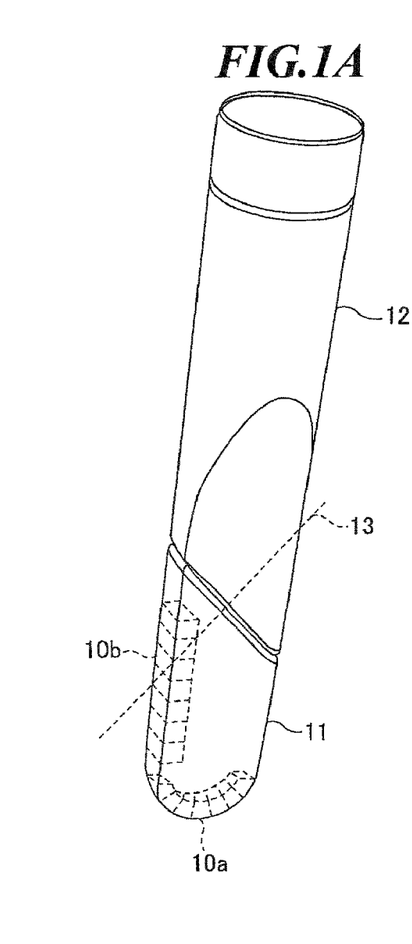
FIGS. 1A-1C are perspective views showing an appearance of an ultrasonic probe according to the first embodiment of the present invention.
Figure 1B:
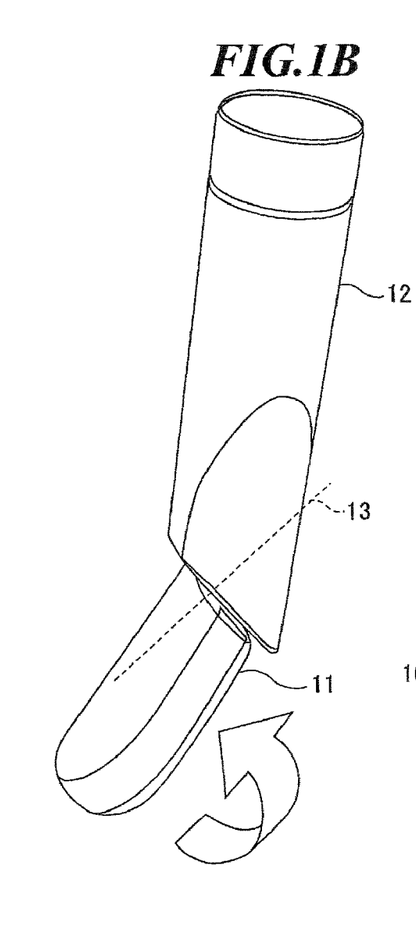
Figure 1C:
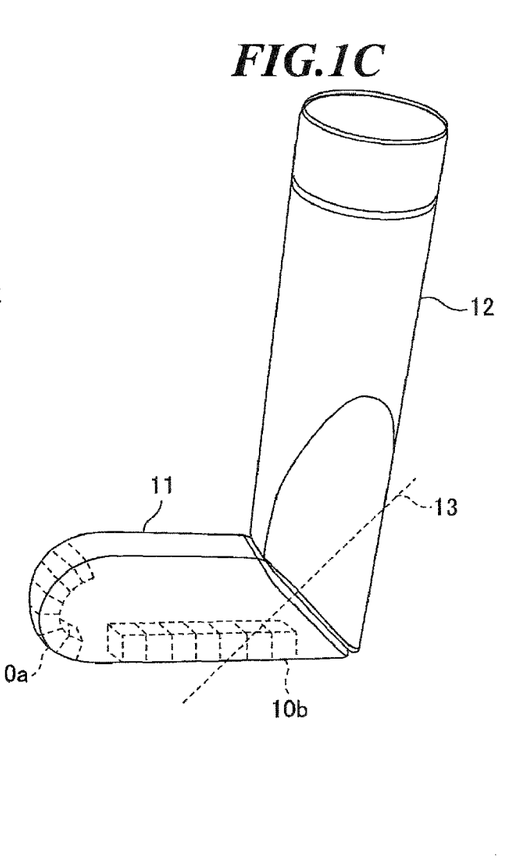

FIGS. 1A-1C are perspective views showing an appearance of an ultrasonic probe according to the first embodiment of the present invention. FIG. 1A shows a state in which an axis direction (longitudinal direction) of a housing part 11 is at the same angle as that of an axis direction (longitudinal direction) of a grip part 12, FIG. 1B shows a state in which the housing part 11 is on the way of rotation relative to the grip part 12, and FIG. 1C shows a state in which the axis direction of the housing part 11 is at an angle perpendicular to the axis direction of the grip part 12.

As shown in FIGS. 1A-1C, the ultrasonic probe includes the housing part 11 for housing a first group of ultrasonic transducers forming a first transducer array 10a and a second group of ultrasonic transducers forming a second transducer array 10b, and the grip part 12 to be gripped by an operator at operation of the ultrasonic probe. The housing part 11 has a stick shape with a rectangular section perpendicular to the axis direction (longitudinal direction), linear edge lines along the axis direction, and an arc edge line of the leading end. The grip part 12 also has a stick shape. Its section perpendicular to the axis direction (longitudinal direction) is rectangular near the joint surface to the housing part 11, changes in shape according to a distance away from the joint surface, and becomes circular in the part farthest from the joint surface.

The first transducer array 10a includes the first group of ultrasonic transducers arranged in an arc form, and housed in an arc-shaped first edge part located on the leading end of the housing part 11. The second transducer array 10b includes the second group of ultrasonic transducers arranged in a linear form, and housed in a linear second edge part along the axis direction of the housing part 11. Note that the arrangement of the second group of ultrasonic transducers is not necessarily linear. For example, the second group of ultrasonic transducers may be arranged along a curve having a curvature different from that of a curve along the arrangement of the first group of ultrasonic transducers.

The housing part 11 and the grip part 12 are rotatably journaled (supported around a support shaft 13) relative to each other, and the support shaft 13 is provided at an angle of 45° obliquely relative to the axis direction of the grip part 12. Accordingly, by rotating the housing part 11 by 180° relative to the grip part 12 around the support shaft 13, the ultrasonic probe is changeable between the state (FIG. 1A) in which the axis direction of the housing part 11 is at the same angle (a first predetermined angle) as that of the axis direction of the grip part 12 and the state (FIG. 1C) in which the axis direction of the housing part 11 is at the angle (a second predetermined angle) perpendicular to the axis direction of the grip part 12. According to the configuration, the operator of the ultrasonic diagnostic apparatus can easily switch between the first predetermined angle and the second predetermined angle. Further, since the section of the housing part 11 is rectangular, the operator can easily switch between the first predetermined angle and the second predetermined angle by putting his or her finger on the edge line of the housing part 11.

In the state (FIG. 1A) in which the axis direction of the housing part 11 is at the same angle as that of the axis direction of the grip part 12, the first transducer array 10a is located farthest in the axis direction of the grip part 12, and thus, an ultrasonic image can be generated by transmission and reception of ultrasonic waves using the first transducer array 10a. On the other hand, in the state (FIG. 1C) in which the axis direction of the housing part 11 is at the angle perpendicular to the axis direction of the grip part 12, the second transducer array 10b is located farthest in the axis direction of the grip part 12, and thus, an ultrasonic image can be generated by transmission and reception of ultrasonic waves using the second transducer array 10b.

Figure 2:
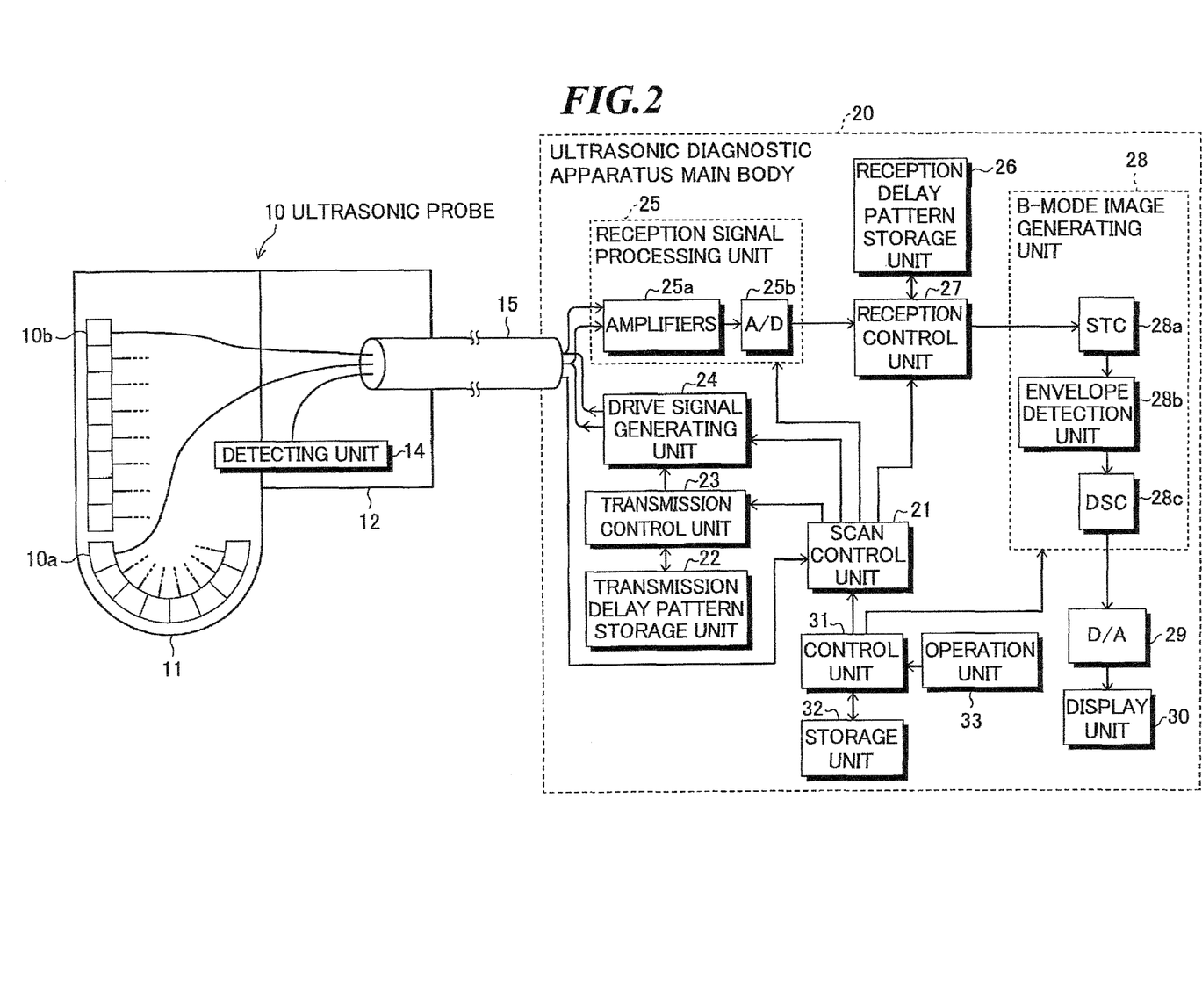
FIG. 2 is a block diagram showing an internal configuration of an ultrasonic diagnostic apparatus according to the first embodiment of the present invention.

Next, an ultrasonic diagnostic apparatus according to the first embodiment of the present invention will be explained. FIG. 2 is a block diagram showing an internal configuration of an ultrasonic diagnostic apparatus according to the first embodiment of the present invention. The ultrasonic diagnostic apparatus includes the ultrasonic probe 10 and an ultrasonic diagnostic apparatus main body 20.

The ultrasonic probe 10 includes the housing part 11 for housing the first transducer array 10a and the second transducer array 10b as described above, the grip part 12 rotatable relative to the housing part 11, and a detecting unit 14 for detecting whether the axis direction of the housing part 11 is at the first predetermined angle or the second predetermined angle relative to the axis direction of the grip part 12. Further, signals are transmitted between the ultrasonic probe 10 and the ultrasonic diagnostic apparatus main body 20 via a cable 15 as signal transmission means.

The first group of ultrasonic transducers forming the first transducer array 10a and the second group of ultrasonic transducers forming the second transducer array 10b transmit ultrasonic waves according to applied drive signals, and receive propagating ultrasonic echoes to output reception signals.

Each ultrasonic transducer includes a vibrator having electrodes formed on both ends of a material having a piezoelectric property (piezoelectric material) such as a piezoelectric ceramic represented by PZT (Pb (lead) zirconate titanate), a polymeric piezoelectric element represented by PVDF (polyvinylidene difluoride), or the like. When a pulsed or continuous wave voltage is applied to the electrodes of the vibrator, the piezoelectric material expands and contracts. By the expansion and contraction, pulse or continuous wave ultrasonic waves are generated from the respective vibrators, and an ultrasonic beam is formed by synthesizing these ultrasonic waves. Further, the respective vibrators expand and contract by receiving the propagating ultrasonic waves to generate electric signals. These electric signals are outputted as reception signals of ultrasonic waves.

The detecting unit 14 detects whether the axis direction of the housing part 11 is at the same angle (the first predetermined angle) as that of the axis direction of the grip part 12 or at the angle (the second predetermined angle) perpendicular to the axis direction of the grip part 12, and outputs a detection result as a detection signal. The detection signal is received by a scan control unit 21 of the ultrasonic diagnostic apparatus main body 20, which will be described later, via the cable 15.

The cable 15 includes many signal wires (typically, coaxial cables are used) for connecting the first group of ultrasonic transducers forming the first transducer array 10a to the ultrasonic diagnostic apparatus main body 20, many signal wires (typically, coaxial cables are used) for connecting the second group of ultrasonic transducers forming the second transducer array 10b to the ultrasonic diagnostic apparatus main body 20, and a signal wire (typically, a single-wire cable is used) for connecting the detecting unit 14 to the ultrasonic diagnostic apparatus main body 20. In FIG. 2, only one signal wire is shown with respect to one transducer array 10a or 10b, and the signal wires connected to the individual ultrasonic transducers are omitted.

The ultrasonic diagnostic apparatus main body 20 includes the scan control unit 21, a transmission delay pattern storage unit 22, a transmission control unit 23, a drive signal generating unit 24, a reception signal processing unit 25, a reception delay pattern storage unit 26, a reception control unit 27, a B-mode image generating unit 28, a D/A converter 29, a display unit 30, a control unit 31, a storage unit 32, and an operation unit 33.

The scan control unit 21 selects one of the first transducer array 10a and the second transducer array 10b to be driven, according to the detection signal outputted from the detecting unit 14. That is, the scan control unit 21 selects the first transducer array 10a in the state in which the axis direction of the housing part 11 is at the same angle as that of the axis direction of the grip part 12, and selects the second transducer array 10b in the state in which the axis direction of the housing part 11 is at the angle perpendicular to the axis direction of the grip part 12. Further, the scan control unit 21 selects or sets an appropriate drive frequency and scan mode corresponding to the selected first or second transducer array 10a or 10b. Then, the scan control unit 21 sequentially sets the transmission direction of an ultrasonic beam and the reception direction of ultrasonic echoes with respect to the selected first or second transducer array 10a or 10b.

The transmission delay pattern storage unit 22 has stored plural transmission delay patterns to be used when an ultrasonic beam is formed. The transmission control unit 23 selects a transmission delay pattern from among the plural transmission delay patterns stored in the transmission delay pattern storage unit 22 according to the transmission direction set by the scan control unit 21, and sets delay times to be respectively provided to drive signals for the plural ultrasonic transducers forming the first or second transducer array 10a or 10b selected by the scan control unit 21 based on the selected transmission delay pattern. Alternatively, the transmission control unit 23 may set delay times such that the ultrasonic waves transmitted at a time from the plural ultrasonic transducers forming the selected first or second transducer array 10a or 10b reach an entire imaging region of the object.

The drive signal generating unit 24 includes plural pulsers corresponding to the plural ultrasonic transducers forming the first or second transducer array 10a or 10b, for example. The drive signal generating unit 24 supplies drive signals to the plural ultrasonic transducers such that the ultrasonic waves transmitted from the plural ultrasonic transducers forming the first or second transducer array 10a or 10b selected by the scan control unit 21 form an ultrasonic beam according to the delay times set by the transmission control unit 23, or supplies drive signals to the plural ultrasonic transducers such that the ultrasonic waves transmitted at a time from the ultrasonic transducers reach the entire imaging region of the object.

The reception signal processing unit 25 includes plural preamplifiers 25a and plural A/D converters 25b corresponding to the plural ultrasonic transducers forming the first or second transducer array 10a or 10b. The reception signals outputted from the plural ultrasonic transducers forming the first or second transducer array 10a or 10b selected by the scan control unit 21 are amplified by the amplifiers 25a and the analog reception signals outputted from the amplifiers 25a are converted into digital reception signals by the A/D converters 25b. The A/D converters 25b output the digital reception signals to the reception control unit 27.

The reception delay pattern storage unit 26 has stored plural reception delay patterns to be used when reception focusing processing is performed on the plural reception signals outputted from the plural ultrasonic transducers. The reception control unit 27 selects a reception delay pattern from among the plural reception delay patterns stored in the reception delay pattern storage unit 26 according to the reception direction set by the scan control unit 21, and performs reception focusing processing by providing delays to the plural reception signals based on the selected reception delay pattern and adding the signals to one another. By the reception focusing processing, a sound ray signal is formed in which the focus of the ultrasonic echoes is narrowed.

The B-mode image generating unit 28 generates a B-mode image signal as tomographic image information on tissues within the object based on the sound ray signal formed by the reception control unit 27. The B-mode image generating unit 28 includes an STC (sensitivity time control) unit 28a, an envelope detection unit 28b, and a DSC (digital scan converter) 28c.

The STC unit 28a performs correction of attenuation due to distance according to the depths of the reflection positions of ultrasonic waves on the sound ray signal formed by the reception control unit 27. The envelope detection unit 28b performs envelope detection processing on the sound ray signal corrected by the STC unit 28a to generate an envelope signal. The DSC 28c converts (raster-converts) the envelope signal generated by the envelope detection unit 28b into an image signal that follow the normal scan system of television signals and performs necessary image processing such as gradation processing to generate a B-mode image signal.

The D/A converter 29 converts the digital image signal outputted from the B-mode image generating unit 28 into an analog image signal. The display unit 30 includes a display device such as a CRT, LCD, or the like, and displays a diagnostic image based on the analog image signal.

The control unit 31 controls the scan control unit 21, B-mode image generating unit 28, and so on according to the operation by the operator using the operation unit 33. In the embodiment, the scan control unit 21, transmission control unit 23, reception control unit 27, B-mode image generating unit 28, and control unit 31 are formed of a CPU and software (program), however, they may be formed of digital circuits or analog circuits. The software is stored in the storage unit 32. As a recording medium in the storage unit 73, not only a built-in hard disk but also a flexible disk, MO, MT, RAM, CD-ROM, DVD-ROM, or the like may be used.

According to the embodiment, since one of the first and second transducer arrays 10a and 10b is selectively driven in response to the detection signal outputted from the detecting unit 14, the first transducer array 10a and the second transducer array 10b can be switched only by changing the angle between the axis direction of the housing part 11 and the axis direction of the grip part 12.

Further, the ultrasonic diagnostic apparatus main body 20 drives the first transducer array 10a located farthest in the axis direction of the grip part 12 in the state in which the axis direction of the housing part 11 is at the same angle as that of the axis direction of the grip part 12, and drives the second transducer array 10b located farthest in the axis direction of the grip part 12 in the state in which the axis direction of the housing part 11 is at the angle perpendicular to the axis direction of the grip part 12. At this time, by positioning the ultrasonic transducers to be used in the farthest part in the axis direction of the grip part 12, the edge part of the housing part 11 for housing the ultrasonic transducers to be used can easily be pressed onto an object to be inspected against the reaction force from the object.

Furthermore, since the ultrasonic diagnostic apparatus main body 20 selects an appropriate drive frequency according to the selection of one of the first transducer array 10a and the second transducer array 10b, a drive frequency can be changed to the appropriate drive frequency only by changing the angle between the axis direction of the housing part 11 and the axis direction of the grip part 12, and the effort of the operation by the operator can be reduced.

Next, an ultrasonic diagnostic apparatus according to the second embodiment of the present invention will be explained.

Figure 3:
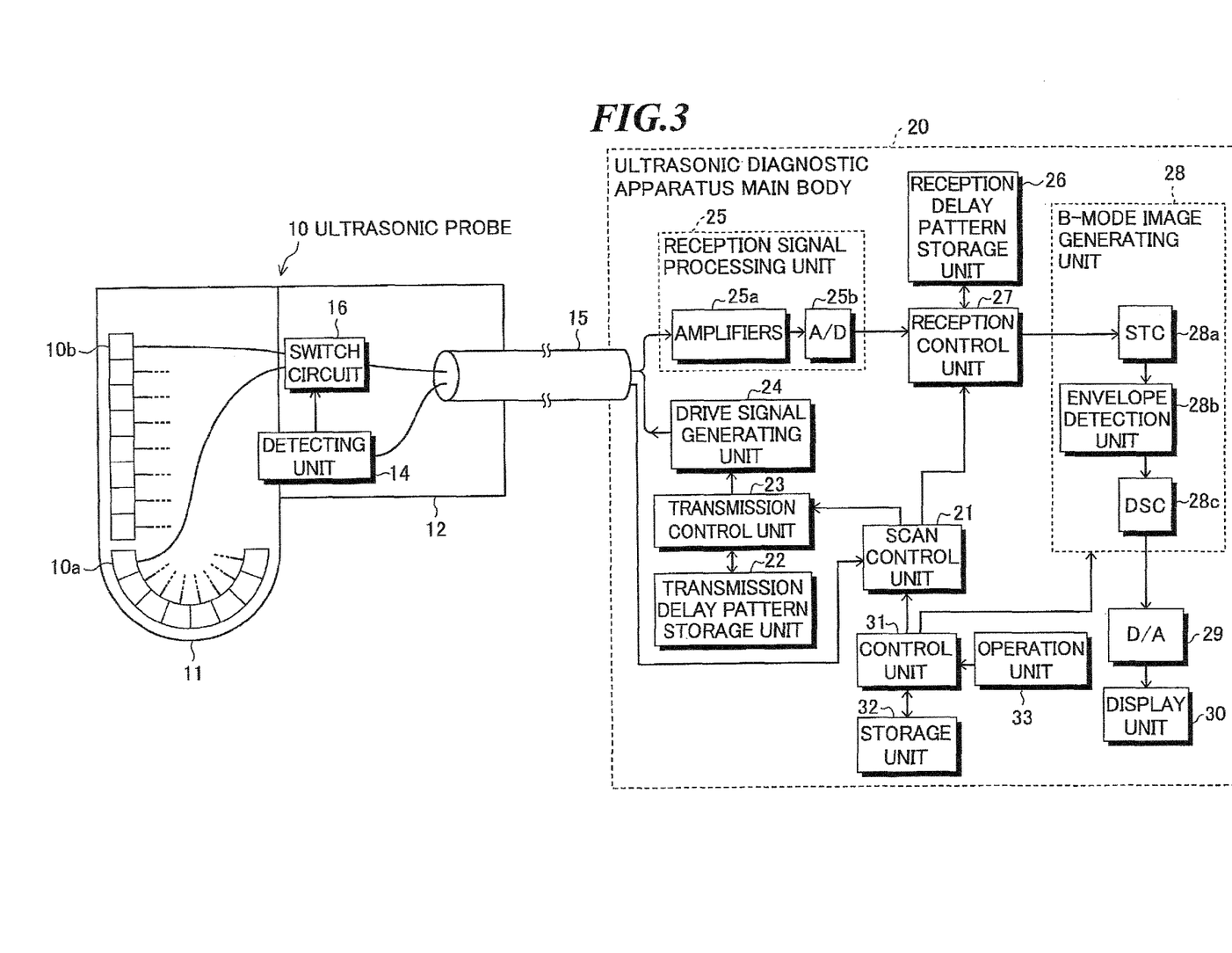
FIG. 3 is a block diagram showing an internal configuration of an ultrasonic diagnostic apparatus according to the second embodiment of the present invention.

FIG. 3 is a block diagram showing an internal configuration of the ultrasonic diagnostic apparatus according to the second embodiment of the present invention. In the second embodiment, the ultrasonic probe 10 further includes a switch circuit 16.

The switch circuit 16 is a circuit for selectively connecting one of the first transducer array 10a and the second transducer array 10b to the signal wires within the cable 15. The switch circuit 16 switches the connection status according to the detection signal outputted from the detecting unit 14, that is, according to whether the axis direction of the housing part 11 is at the same angle (the first predetermined angle) as that of the axis direction of the grip part 12 or at the angle (the second predetermined angle) perpendicular to the axis direction of the grip part 12.

Specifically, when the axis direction of the housing part 11 is at the same angle as that of the axis direction of the grip part 12, the switch circuit 16 connects the first transducer array 10a located farthest in the axis direction of the grip part 12 to the signal wires within the cable 15, and, when the axis direction of the housing part 11 is at the angle perpendicular to the axis direction of the grip part 12, the switch circuit 16 connects the second transducer array 10b located farthest in the axis direction of the grip part 12 to the signal wires within the cable 15.

According to the embodiment, it is not necessary to separately provide the signal wires corresponding to the first transducer array 10a and the signal wires corresponding to the second transducer array 10b within the cable 15, and the cable 15 can be made thinner. The rest is the same as that in the first embodiment as shown in FIGS. 1A-2.

Next, an ultrasonic diagnostic apparatus according to the third embodiment of the present invention will be explained.

Figure 4:
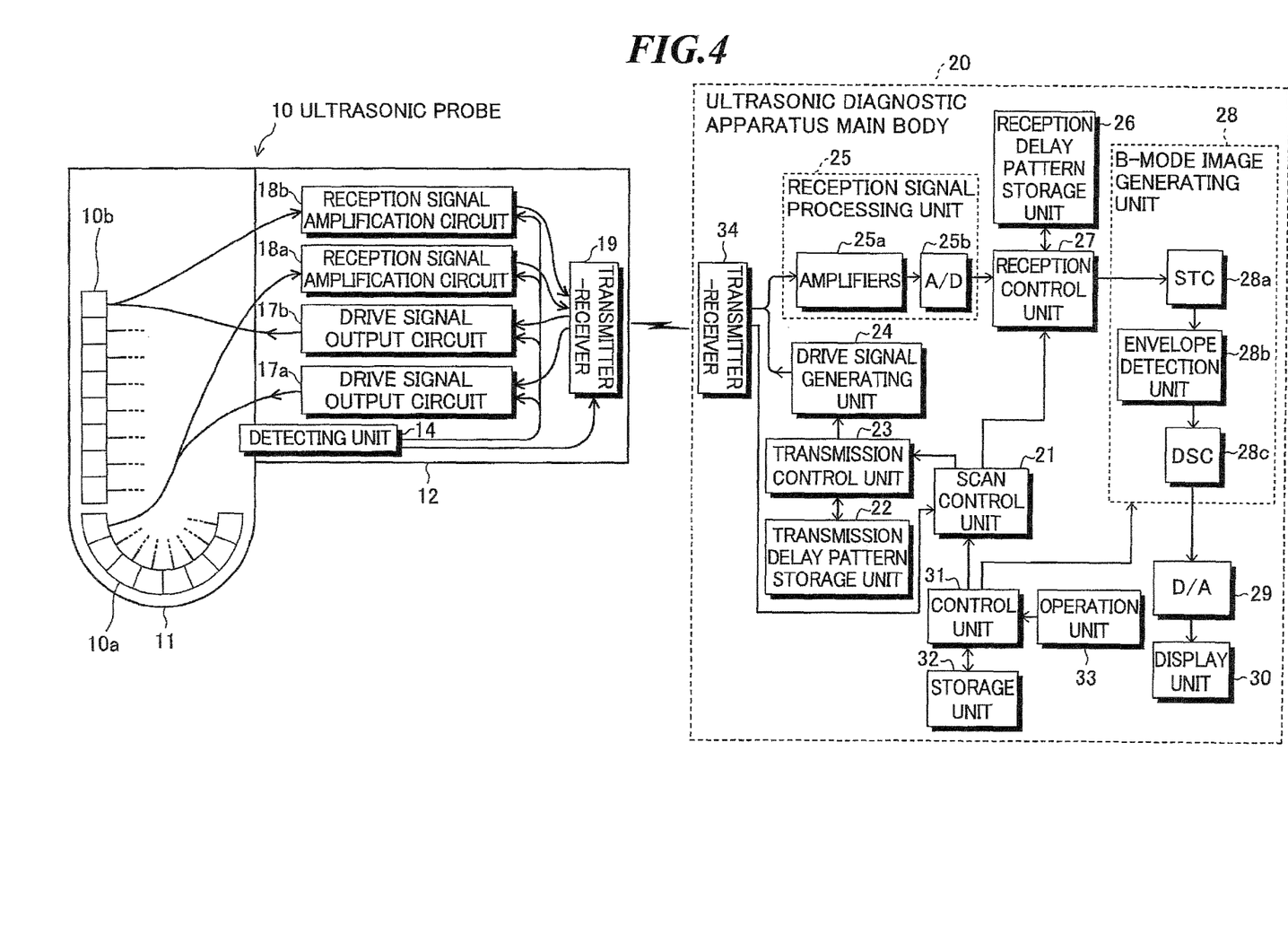
FIG. 4 is a block diagram showing an internal configuration of an ultrasonic diagnostic apparatus according to the third embodiment of the present invention.

FIG. 4 is a block diagram showing an internal configuration of the ultrasonic diagnostic apparatus according to the third embodiment of the present invention. In the third embodiment, signals are wirelessly transmitted between the ultrasonic probe 10 and the ultrasonic diagnostic apparatus main body 20. For the purpose, the ultrasonic probe 10 further includes a transmitter-receiver 19, and the ultrasonic diagnostic apparatus main body 20 further includes a transmitter-receiver 34. The transmitter-receivers 19 and 34 as signal transmission means are wireless communication tools using any kind of carrier such as electromagnetic wave, magnetic field, and infrared ray. Further, the ultrasonic probe 10 further includes drive signal output circuits 17a and 17b, reception signal amplification circuits 18a and 18b, and a battery (rechargeable battery or the like) for supplying a power supply voltage to the circuits within the ultrasonic probe 10.

The transmitter-receiver 34 transmits drive signals outputted from the drive signal generating unit 24 to the transmitter-receiver 19. The transmitter-receiver 19 supplies the received drive signals to the drive signal output circuit 17a when the first transducer array 10a is used, and supplies the received drive signals to the drive signal output circuit 17b when the second transducer array 10b is used.

Further, the transmitter-receiver 19 transmits the reception signals outputted from the reception signal amplification circuit 18a to the transmitter-receiver 34 when the first transducer array 10a is used, and transmits the reception signals outputted from the reception signal amplification circuit 18b to the transmitter-receiver 34 when the second transducer array 10b is used. Furthermore, the transmitter-receiver 19 transmits the detection signal outputted from the detecting unit 14 to the transmitter-receiver 34. The transmitter-receiver 34 outputs the reception signals received from the transmitter-receiver 19 to the reception signal processing unit 25 and the detection signal received from the transmitter-receiver 19 to the scan control unit 21.

When the first transducer array 10a is used, the drive signal output circuit 17a amplifies the drive signals supplied from the transmitter-receiver 19 to have power necessary for driving the ultrasonic transducers, and outputs the amplified drive signals. When the second transducer array 10b is used, the drive signal output circuit 17b amplifies the drive signals supplied from the transmitter-receiver 19 to have power necessary for driving the ultrasonic transducers, and outputs the amplified drive signals. The drive signals amplified by the drive signal output circuit 17a are outputted to the first group of ultrasonic transducers included in the first transducer array 10a, and the drive signals amplified by the drive signal output circuit 17b are outputted to the second group of ultrasonic transducers included in the second transducer array 10b.

When the first transducer array 10a is used, the reception signal amplification circuit 18a amplifies the reception signals outputted from the first group of ultrasonic transducers included in the first transducer array 10a, and outputs the amplified reception signals to the transmitter-receiver 19. When the second transducer array 10b is used, the reception signal amplification circuit 18b amplifies the reception signals outputted from the second group of ultrasonic transducers included in the second transducer array 10b and outputs the amplified reception signals to the transmitter-receiver 19.

According to the embodiment, since the signals are transmitted between the ultrasonic probe 10 and the ultrasonic diagnostic apparatus main body 20, at an ultrasonic diagnosis, the operator can concentrate his or her attention on the diagnosis without regard to handling of the cable. The rest is the same as that in the first embodiment as shown in FIGS. 1A-2.

Next, an ultrasonic diagnostic apparatus according to the fourth embodiment of the present invention will be explained.

Figure 5:
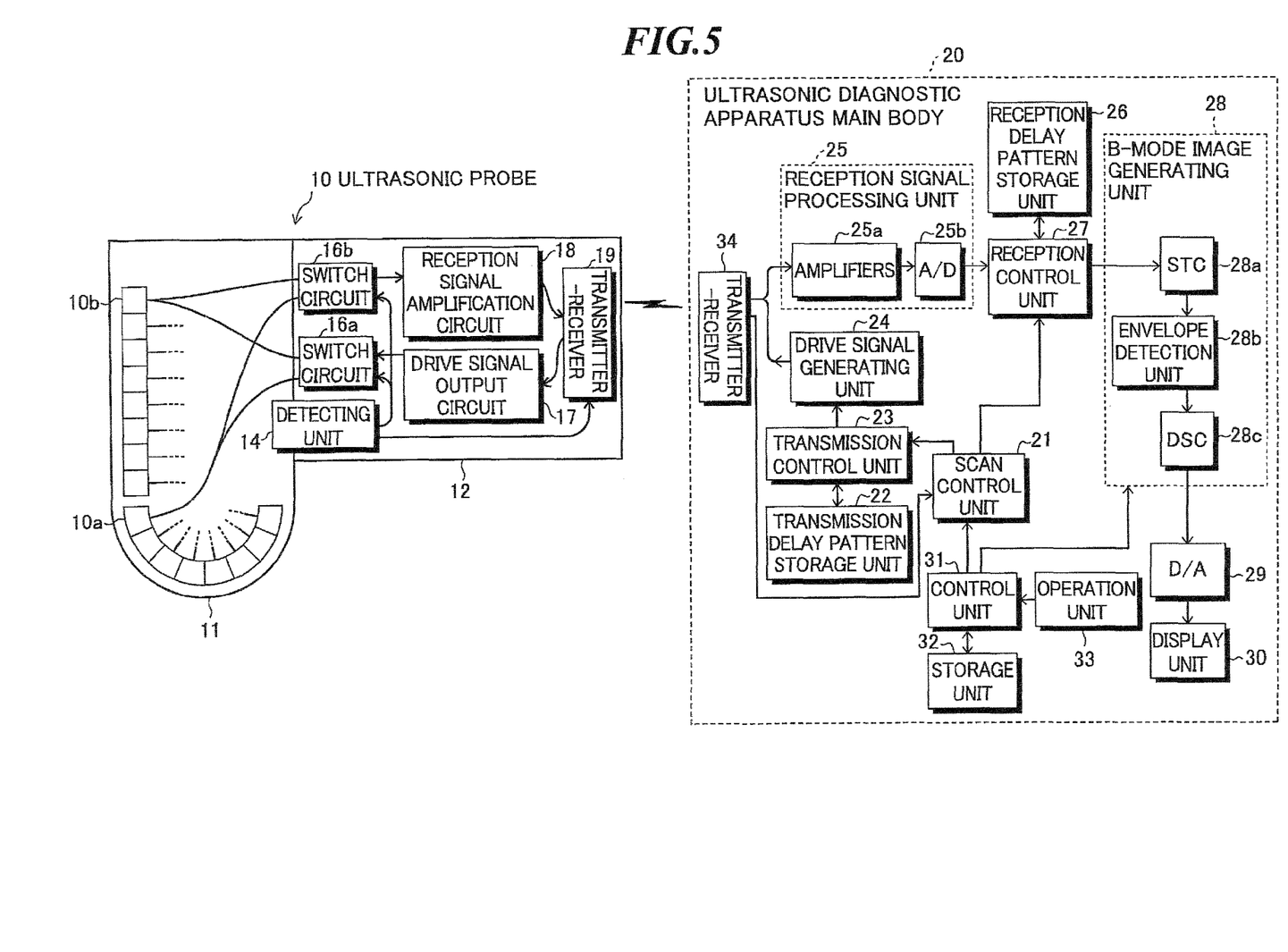
FIG. 5 is a block diagram showing an internal configuration of an ultrasonic diagnostic apparatus according to the fourth embodiment of the present invention.

FIG. 5 is a block diagram showing an internal configuration of the ultrasonic diagnostic apparatus according to the fourth embodiment of the present invention. In the fourth embodiment, the ultrasonic probe 10 further includes switch circuits 16a and 16b. Thereby, the drive signal output circuit 17 is commonly used for driving the first transducer array 10a and for driving the second transducer array 10b. Further, the reception signal amplification circuit 18 is commonly used for amplifying reception signals of the first transducer array 10a and for amplifying reception signals of the second transducer array 10b.

The switch circuit 16a is a circuit for selectively connecting one of the first transducer array 10a and the second transducer array 10b to the drive signal output circuit 17. Further, the switch circuit 16b is a circuit for selectively connecting one of the first transducer array 10a and the second transducer array 10b to the reception signal amplification circuit 18.

These switch circuits 16a and 16b switch the connection status according to the detection signal outputted from the detecting unit 14, that is, according to whether the axis direction of the housing part 11 is at the same angle (the first predetermined angle) as that of the axis direction of the grip part 12 or at the angle (the second predetermined angle) perpendicular to the axis direction of the grip part 12.

Specifically, when the axis direction of the housing part 11 is at the same angle as that of the axis direction of the grip part 12, the switch circuits 16a and 16b connect the first transducer array 10a located farthest in the axis direction of the grip part 12 to the drive signal output circuit 17 and the reception signal amplification circuit 18, and, when the axis direction of the housing part 11 is at the angle perpendicular to the axis direction of the grip part 12, the switch circuits 16a and 16b connect the second transducer array 10b located farthest in the axis direction of the grip part 12 to the drive signal output circuit 17 and the reception signal amplification circuit 18.

According to the embodiment, it is not necessary to separately provide the drive signal output circuits and the reception signal amplification circuits corresponding to the plural ultrasonic transducer arrays within the ultrasonic probe 10, and the ultrasonic probe 10 can be made smaller and simpler. The rest is the same as that in the third embodiment as shown in FIG. 4.

Next, an ultrasonic probe according to the fifth embodiment of the present invention will be explained.

Figure 6:
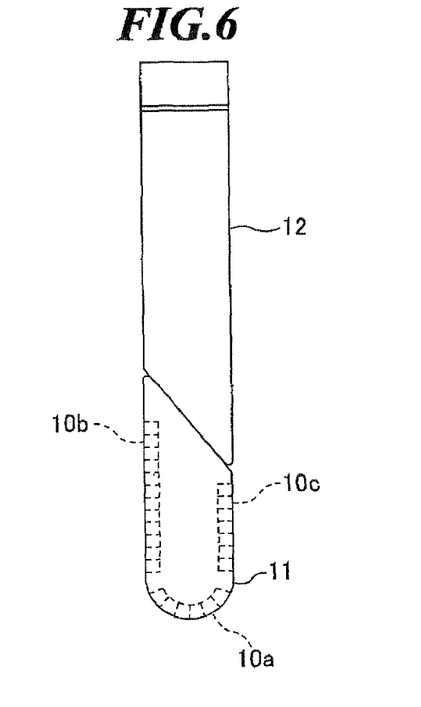
FIG. 6 is a front view showing an appearance of an ultrasonic probe according to the fifth embodiment of the present invention.

FIG. 6 is a front view showing an appearance of the ultrasonic probe according to the fifth embodiment of the present invention, and shows the state in which the axis direction of the housing part 11 is at the same angle as that of the axis direction of the grip part 12. In the embodiment, the housing part 11 of the ultrasonic probe further includes a third transducer array 10c in addition to the first transducer array 10a and the second transducer array 10b.

Here, the first transducer array 10a includes plural ultrasonic transducers arranged in an arc form. On the other hand, each of the second transducer array 10b and the third transducer array 10c includes plural ultrasonic transducers arranged in linear forms. Note that, in the third transducer array 10c, the plural ultrasonic transducers are provided in a region narrower than that of the second transducer array 10b.

According to the configuration, by selecting one transducer array from among the three transducer arrays 10a, 10b, and 10c and driving it, the most appropriate transducer array can be employed according to the part of the object to be diagnosed. The rest is the same as that in the first embodiment as shown in FIGS. 1A-2. Further, the internal configurations of the second to fourth embodiments shown in FIGS. 3-5 may be applied.

Next, an ultrasonic probe according to the sixth embodiment of the present invention will be explained.

Figure 7:
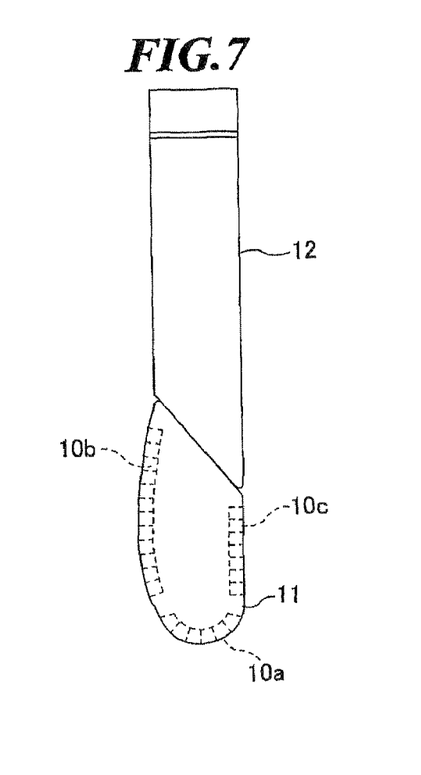
FIG. 7 is a front view showing an appearance of an ultrasonic probe according to the sixth embodiment of the present invention.

FIG. 7 is a front view showing an appearance of the ultrasonic probe according to the sixth embodiment of the present invention, and shows the state in which the axis direction of the housing part 11 is at the same angle as that of the axis direction of the grip part 12. In the embodiment, the housing part 11 of the ultrasonic probe further includes a third transducer array 10c in addition to the first transducer array 10a and the second transducer array 10b.

Here, each of the first transducer array 10a and the second transducer array 10b includes plural ultrasonic transducers arranged in arc forms. Note that, the second transducer array 10b is provided in an arc form gentler than that of the first transducer array 10a. On the other hand, the third transducer array 10c includes plural ultrasonic transducers arranged in a linear form.

According to the configuration, by selecting one transducer array from among the three transducer arrays 10a, 10b, and 10c and driving it, the most appropriate ultrasonic transducers can be employed according to the part of the object to be diagnosed. The rest is the same as that in the first embodiment as shown in FIGS. 1A-2. Further, the internal configurations of the second to fourth embodiments shown in FIGS. 3-5 may be applied.

Next, an ultrasonic probe according to the seventh embodiment of the present invention will be explained.

Figure 8A:
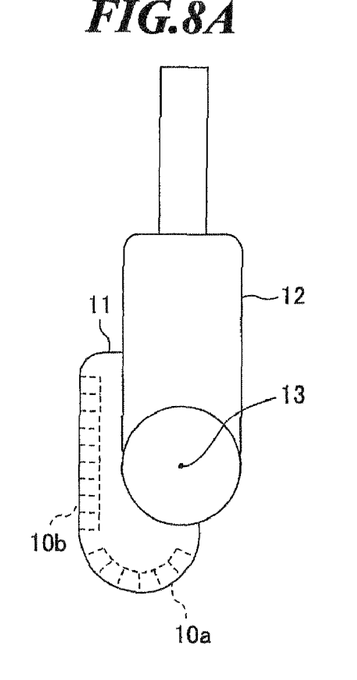
FIGS. 8A and 8B are front views showing an appearance of an ultrasonic probe according to the seventh embodiment of the present invention.
Figure 8B:
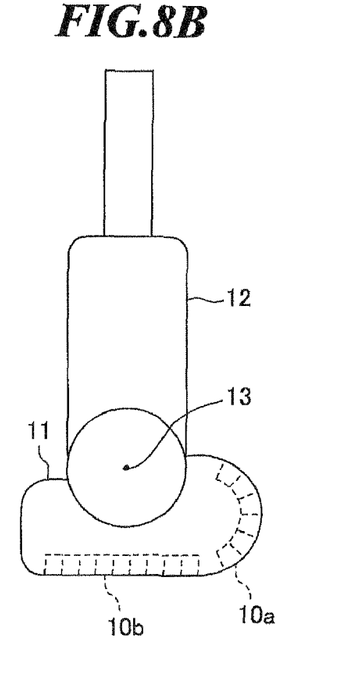

FIGS. 8A and 8B are front views showing an appearance of the ultrasonic probe according to the seventh embodiment of the present invention. FIG. 8A shows the state in which the axis direction of the housing part 11 is at the same angle as that of the axis direction of the grip part 12, and FIG. 8B shows the state in which the axis direction of the housing part 11 is at the angle perpendicular to the axis direction of the grip part 12.

In the embodiment, the support shaft 13 for rotatably journaling the housing part 11 and the grip part 12 of the ultrasonic probe relative to each other is provided perpendicular to the axis direction of the grip part 12. Accordingly, by rotating the housing part 11 by 90° relative to the grip part 12 around the support shaft 13, the ultrasonic probe is changeable between the state (FIG. 8A) in which the axis direction of the housing part 11 is at the same angle (a first predetermined angle) as that of the axis direction of the grip part 12 and the state (FIG. 8B) in which the axis direction of the housing part 11 is at the angle (a second predetermined angle) perpendicular to the axis direction of the grip part 12.

In the state (FIG. 8A) in which the axis direction of the housing part 11 is at the same angle as that of the axis direction of the grip part 12, the first transducer array 10a is located farthest in the axis direction of the grip part 12. On the other hand, in the state (FIG. 8B) in which the axis direction of the housing part 11 is at the angle perpendicular to the axis direction of the grip part 12, the second transducer array 10b is located farthest in the axis direction of the grip part 12.

According to the configuration, the most appropriate ultrasonic transducers can be employed according to the part of the object to be diagnosed. The rest is the same as that in the first embodiment as shown in FIGS. 1A-2. Further, the internal configurations of the second to fourth embodiments shown in FIGS. 3-5 may be applied.

Next, an ultrasonic probe according to the eighth embodiment of the present invention will be explained.

Figure 9A:
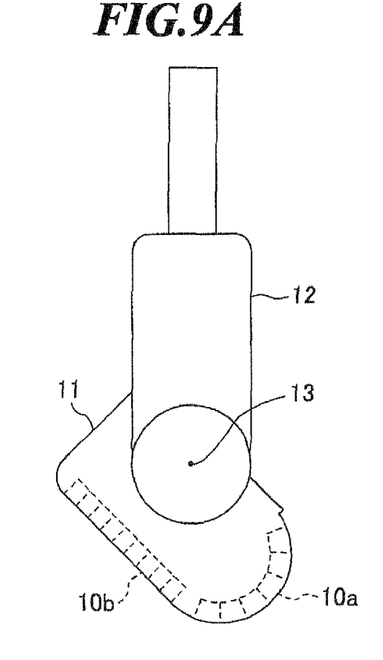
FIGS. 9A and 9B are front views showing an appearance of an ultrasonic probe according to the eighth embodiment of the present invention.
Figure 9B:
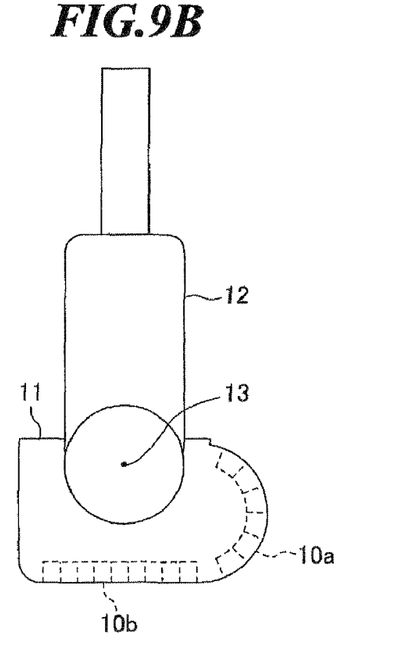

FIGS. 9A and 9B are front views showing an appearance of the ultrasonic probe according to the eighth embodiment of the present invention. FIG. 9A shows the state in which the axis direction of the housing part 11 is at an angle slightly tilted from the axis direction of the grip part 12, and FIG. 9B shows the state in which the axis direction of the housing part 11 is at the angle perpendicular to the axis direction of the grip part 12.

Also in the embodiment, the support shaft 13 for rotatably journaling the housing part 11 and the grip part 12 of the ultrasonic probe relative to each other is provided perpendicular to the axis direction of the grip part 12. Accordingly, by rotating the housing part 11 relative to the grip part 12 around the support shaft 13, the ultrasonic probe is changeable between the state (FIG. 9A) in which the axis direction of the housing part 11 is at an angle (a first predetermined angle) slightly tilted from the axis direction of the grip part 12 and the state (FIG. 9B) in which the axis direction of the housing part 11 is at the angle (a second predetermined angle) perpendicular to the axis direction of the grip part 12.

Thus, the first predetermined angle may not necessarily be 0° at which the axis direction of the housing part 11 is at the same angle as that of the axis direction of the grip part 12, but may be an angle slightly tilted. Further, the second predetermined angle may not necessarily be 90° at which the axis direction of the housing part 11 is at the angle perpendicular to the axis direction of the grip part 12. Furthermore, the difference between the first predetermined angle and the second predetermined angle may not be 90°. According to the configuration, the most appropriate ultrasonic transducers can be employed according to the part of the object to be diagnosed. The rest is the same as that in the seventh embodiment as shown in FIGS. 8A and 8B.

The invention claimed is:

1. An ultrasonic probe comprising:
   a housing part for housing a first group of ultrasonic transducers and a second group of ultrasonic transducers in a first edge part and a second edge part having different curvatures from each other, respectively, said first and second groups of ultrasonic transducers transmitting ultrasonic waves according to drive signals and receiving ultrasonic echoes to output reception signals;
   a grip part rotatable relative to said housing part;
   a detecting unit for detecting whether an axis direction of said housing part is at a first predetermined angle or a second predetermined angle relative to an axis direction of said grip part;
   signal transmission means for transmitting and receiving signals between said ultrasonic probe and an ultrasonic diagnostic apparatus main body; and
   a switch circuit for connecting said signal transmission means to said first group of ultrasonic transducers when the axis direction of said housing part is at the first predetermined angle relative to the axis direction of said grip part, and connecting said signal transmission means to said second group of ultrasonic transducers when the axis direction of said housing part is at the second predetermined angle relative to the axis direction of said grip part according to a detection result of said detecting unit.

2. The ultrasonic probe according to claim 1, wherein:
   said first group of ultrasonic transducers are located farthest in the axis direction of said grip part when the axis direction of said housing part is at the first predetermined angle relative to the axis direction of said grip part; and
   said second group of ultrasonic transducers are located farthest in the axis direction of said grip part when the axis direction of said housing part is at the second predetermined angle relative to the axis direction of said grip part.

3. The ultrasonic probe according to claim 1, wherein said housing part is rotatably supported around a rotational axis provided obliquely relative to the axis direction of said grip part, and the axis direction of said housing part changes its angle relative to the axis direction of said grip part by the rotation around the rotational axis.

4. An ultrasonic diagnostic apparatus comprising:
   an ultrasonic probe including a housing part for housing a first group of ultrasonic transducers and a second group of ultrasonic transducers in a first edge part and a second edge part having different curvatures from each other, respectively, said first and second groups of ultrasonic transducers transmitting ultrasonic waves according to drive signals and receiving ultrasonic echoes to output reception signals, a grip part rotatable relative to said housing part, and a detecting unit for detecting whether an axis direction of said housing part is at a first predetermined angle or a second predetermined angle relative to an axis direction of said grip part; and
   an ultrasonic diagnostic apparatus main body for selectively generating one of a first group of drive signals for driving said first group of ultrasonic transducers and a second group of drive signals for driving said second group of ultrasonic transducers according to a detection result of said detecting unit.

5. The ultrasonic diagnostic apparatus according to claim 4, wherein said ultrasonic diagnostic apparatus main body selectively generates one of the first group of drive signals and the second group of drive signals having different frequencies from each other according to a detection result of said detecting unit.

* * * * *